(12) United States Patent
Middleton-Davis et al.

(10) Patent No.: US 10,288,636 B2
(45) Date of Patent: May 14, 2019

(54) MODULAR FLUID DISPENSING DEVICES

(71) Applicant: Cytoskeleton, Inc., Denver, CO (US)

(72) Inventors: Ashley Middleton-Davis, Denver, CO (US); Kim Middleton-Davis, Denver, CO (US)

(73) Assignee: Cytoskeleton, Inc., Denver, CO (US)

( * ) Notice: Subject to any disclaimer, the term of this patent is extended or adjusted under 35 U.S.C. 154(b) by 0 days.

(21) Appl. No.: 15/427,334

(22) Filed: Feb. 8, 2017

(65) Prior Publication Data

US 2017/0234901 A1     Aug. 17, 2017

Related U.S. Application Data

(63) Continuation of application No. 14/541,708, filed on Nov. 14, 2014, now Pat. No. 9,599,629.

(51) Int. Cl.
| | | |
|---|---|---|
| *G01N 35/10* | (2006.01) |
| *B01L 3/00* | (2006.01) |
| *G01N 33/543* | (2006.01) |
| *G01N 35/00* | (2006.01) |
| *B01L 99/00* | (2010.01) |
| *G01N 33/53* | (2006.01) |
| *B01L 9/00* | (2006.01) |

(52) U.S. Cl.
CPC .......... *G01N 35/1002* (2013.01); *B01L 3/52* (2013.01); *B01L 99/00* (2013.01); *G01N 33/54366* (2013.01); *G01N 35/00* (2013.01); *G01N 35/0092* (2013.01); *G01N 35/00722* (2013.01); *B01L 9/52* (2013.01); *B01L 2200/141* (2013.01); *B01L 2200/16* (2013.01); *B01L 2300/023* (2013.01); *B01L 2400/0457* (2013.01); *B01L 2400/0487* (2013.01); *G01N 33/5302* (2013.01); *G01N 2035/00277* (2013.01)

(58) Field of Classification Search
None
See application file for complete search history.

(56) References Cited

U.S. PATENT DOCUMENTS

| | | |
|---|---|---|
| 4,585,623 A | 4/1986 | Chandler |
| 4,859,419 A | 8/1989 | Marks et al. |
| 4,989,755 A | 2/1991 | Shiau |
| 5,559,032 A | 9/1996 | Pomeroy et al. |
| 5,567,595 A | 10/1996 | Kok |
| 5,674,006 A | 10/1997 | Islam et al. |
| 6,194,160 B1 | 2/2001 | Levin |
| 7,708,946 B1 | 5/2010 | Sherman et al. |
| 7,794,659 B2 | 9/2010 | Lair et al. |

(Continued)

FOREIGN PATENT DOCUMENTS

| | | |
|---|---|---|
| CN | 101923096 | 12/2010 |

OTHER PUBLICATIONS

Bind machine manual; tools.lifetechnologies.com/content/sfs/manuals/ibind_man.pdf, Oct. 2014.

(Continued)

*Primary Examiner* — Kathryn Wright (74) *Attorney, Agent, or Firm* — Stradley Ronon Stevens & Young, LLP (57) ABSTRACT

The present disclosure provides devices which deliver fluids from several reservoirs to a reaction vessel and eventually to a waste chamber in a predetermined schedule. The device provides improved simplicity while improving operational robustness and flexibility.

22 Claims, 11 Drawing Sheets

(56) References Cited

U.S. PATENT DOCUMENTS

| | | |
|---|---|---|
| 8,261,950 B2 | 9/2012 | Cittadino et al. |
| 8,404,198 B2 | 3/2013 | Amshey et al. |
| 8,758,687 B2 | 6/2014 | Gorelik et al. |
| 2005/0019898 A1 | 1/2005 | Adey et al. |
| 2014/0293733 A1 | 10/2014 | Hart et al. |

OTHER PUBLICATIONS

Snap i.d. machine manual; emdmillipore.com/US/en/life-science-research/protein-detection-quantification/SNAP-i. i.d.-2.0-Protein-Detection-System-/snap-id-system-western-blotting/m9Wb.qB.wzoAAAFBrt8RRkwt.nav, Jun. 2014.

Figure 10 A) Flow chart of steps

Figure 10 B) Summary of range of number of steps and length of times for programming.

| Step | Repeats | Range of Time (min) | Time Segments for a Preferred Routine (min) |
| --- | --- | --- | --- |
| Blocking | 1 | 10-240 | 60 |
| Wash 1 | 1 | 1-30 | 3 |
| Primary | 1 | 20-900 | 60 |
| Wash 2 | 3 to 6 | 1-30 | 5 |
| Secondary | 1 | 20-240 | 60 |
| Wash 3 | 3 to 6 | 1-30 | 5 |

Figure 11

MODULAR FLUID DISPENSING DEVICES

FIELD

The present disclosure is directed, in part, to devices that deliver fluids from several reservoirs to a reaction vessel and eventually to a waste chamber in a predetermined schedule, and to methods of carrying out the same.

BACKGROUND

In the field of analytical chemistry, there is a need for improved liquid dispensing devices to probe samples of interest. In particular, in biochemistry a technique called Western Blot analysis requires the timed application of at least three aqueous solutions to probe a membrane which contains samples of interest. The samples are usually proteins, but can also be DNA or carbohydrates. The samples are usually separated into individual molecular species by SDS-PAGE electrophoresis followed by electroblotting on to the membrane. Direct application of pure or complex samples has also been used by pipetting onto the membrane. The membrane binds the sample molecules due to its hydrophobic nature (PVDF membranes) or covalent cross-linking (nitrocellulose membranes). The membrane can then be probed with various detection procedures which identify the particular chemical of interest. It is this last step that requires sequential application of two to five solutions in a timed schedule.

There are presently four methods of probing the membranes described above: 1) manual application of solutions with several timed incubations over a period of about four hours; 2) automated machines that apply a similar routine as the manual operator; 3) a filter paper capillary device that applies one routine (e.g., iBind device by Life Technologies); and 4) a vacuum based method that moves solutions across a membrane by suction (e.g., SNAP id device by EMD Millipore Inc.). All four approaches aim to achieve a similar routine: first, block the membrane with a non-specific solution of protein, DNA, or carbohydrate, which will reduce background noise in the final result; second, in some scenarios a wash step is included; third, the specific analytical reagent (SAR) or primary reagent is added, which binds to the desired target molecule to be measured; fourth, one to six wash steps to remove excess SAR; fifth, application of a second generic reagent that amplifies the signal of the first; and finally, application of 1 to 6 washes with buffer to remove excess reagent. The membrane is then ready for signal development in colorimetric, fluorescence, radiometric, or luminescence modes.

This six step procedure is very time consuming and labor intensive. The operator has to return to the membrane once per hour in the reagent incubation steps and every 3 to 5 minutes in the wash steps, for a total of between 10 and 17 times. In addition, different operators prefer to run different procedures. For example, a first operator may desire to use 3×5 washes and a 2 hour SAR step and a 1 hour secondary reagent step, whereas a second operator might use a 16 hour SAR and only one wash step.

The machines that have been developed to date allow a user to control wash times and reagent incubation times and address the need for automation. However, the machines are highly complex with various combinations of pumps, pressurized air supply and/or actuators, and require a trained individual to operate them. For example U.S. Pat. Nos. 4,859,419, 8,404,198, 5,567,595, 5,559,032, 6,194,160, 4,585,623, and 8,758,687, as well as iBind machine (internet at: tools.lifetechnologies.com/content/sfs/manuals/ibind_man.pdf) and the Snap id machine (internet at: emdmillipore.com/US/en/life-science-research/protein-detection-quantification/SNAP-i.d.-2.0-Protein-Detection-System-/snap-id-system-western-blotting/m9Wb.qB.wzoAAAFBrt8RRkwt.nav) report various machines, some of which are complicated and/or inflexible and require trained personnel to operate and maintain, which makes operation and repair expensive. Thus, there is a need to reduce complexity and costs of manufacture.

The present disclosure addresses many of the drawbacks of the presently available devices.

SUMMARY

The present disclosure provides liquid dispensing devices comprising: a wash buffer reservoir and at least one reagent reservoir, each reservoir comprising a reservoir control valve, wherein each reservoir control valve is in electrical communication with an electronic control board; a reaction vessel in fluid communication with the wash buffer reservoir and the at least one reagent reservoir, wherein the reaction vessel comprises one or more baffles; a waste tray in fluid communication with the reaction vessel; a motorized cam in physical connection with the reaction vessel; and an optional central pump as described herein.

The present disclosure also provides systems comprising a plurality of devices as described herein.

The present disclosure also provides methods of analyzing a membrane using any of the devices described herein comprising: loading a wash buffer into the wash buffer reservoir; loading a first reagent into one of the at least one reagent reservoirs; optionally loading a second reagent into a different one of the at least one reagent reservoirs; loading the membrane and blocking reagent into the reaction vessel; selecting a routine from the electronic control board; and removing the membrane from the reaction vessel for subsequent signal development and result acquisition.

DESCRIPTION OF EMBODIMENTS

A goal of the present disclosure was to create a low cost alternative to available devices which are flexible in procedures but complicated to program and expensive to purchase, operate and maintain. To realize this goal, a minimalist approach was taken to the design of a plumbing scheme of valves and pumps, utilizing gravitational potential or a central pump to propel liquids through valves and tubes. Due to its simplicity, feedback loops from sensors are not required to maintain robust operation and minimizing components allows the foot print to be dramatically reduced compared to other devices (e.g., U.S. Pat. Nos. 4,859,419, 8,404,198, 5,567,595, 5,559,032, 6,194,160, 4,585,623, and 8,758,687, as well as iBind machine and the Snap id machine. In addition, by utilizing advanced low friction plastics, the design simplifies the method of agitating a membrane.

The device, when configured without a central pump, can be divided into four gravitational levels. The highest level contains the wash reservoir and the at least one reagent reservoir. The second level is at the height of the reservoir control valves. The third level is at the reaction vessel height. The fourth level is where the waste is deposited. By purposely designing these levels with similar heights it is possible to create a reliable flow of liquid between any two stages while stopping and starting the flow with a valve control.

Figure 1:
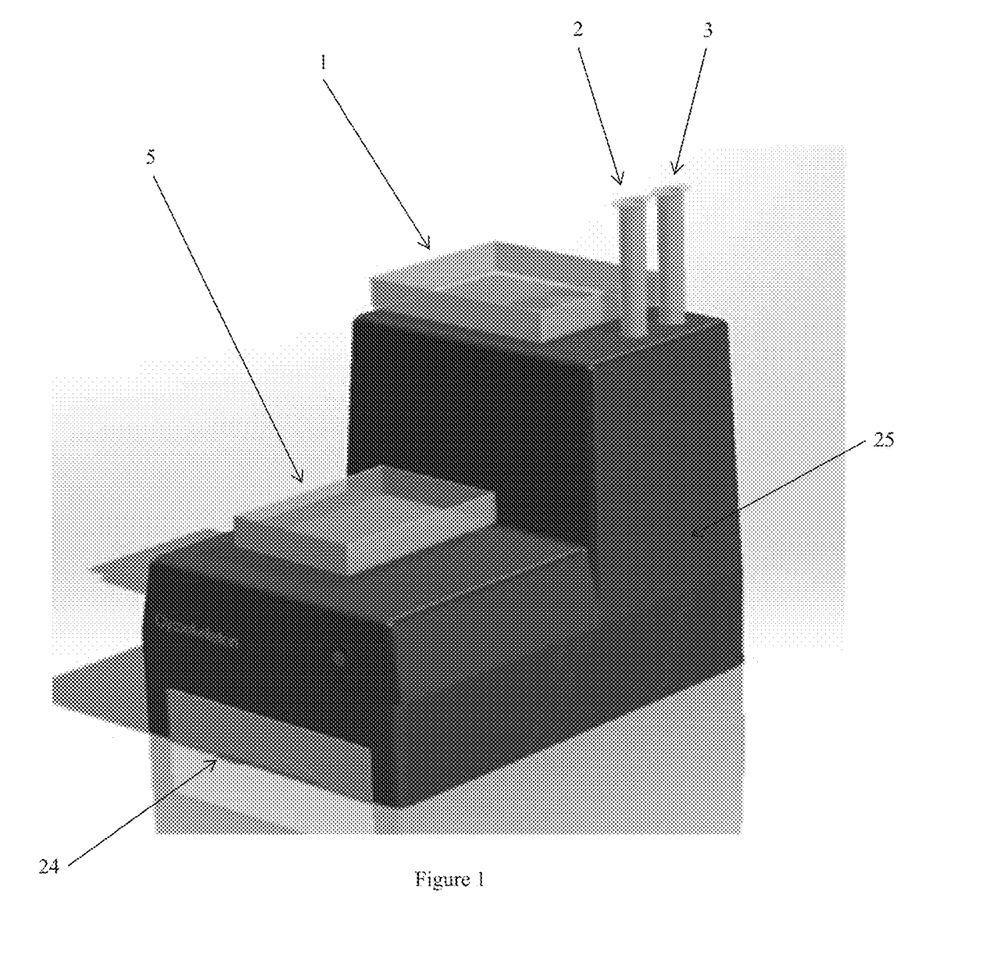
FIG. 1 shows a representative CAD 3D schematic of a device.
Figure 2:
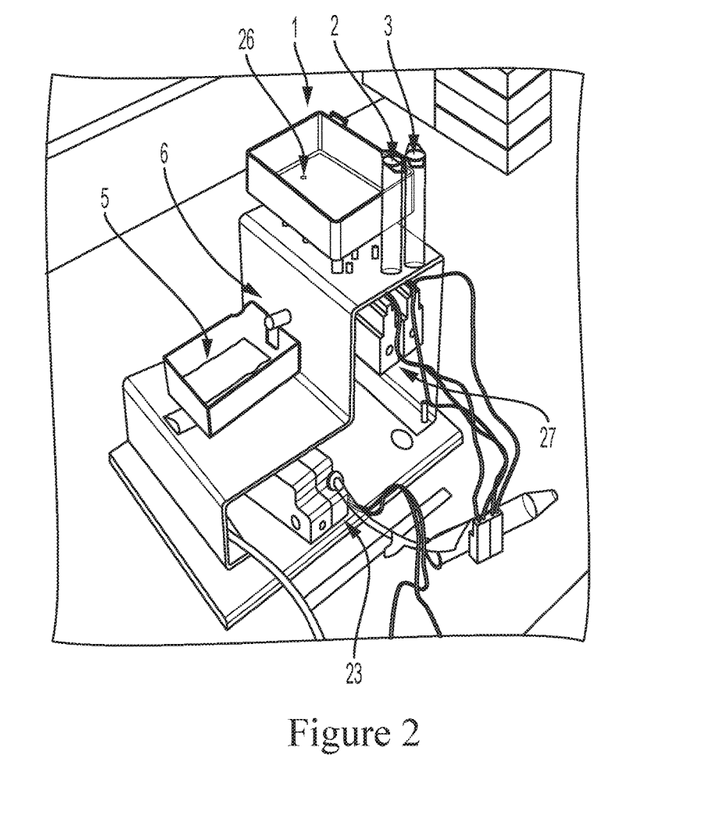
FIG. 2 shows a representative device without a chassis cover revealing several internal components.
Figure 3:
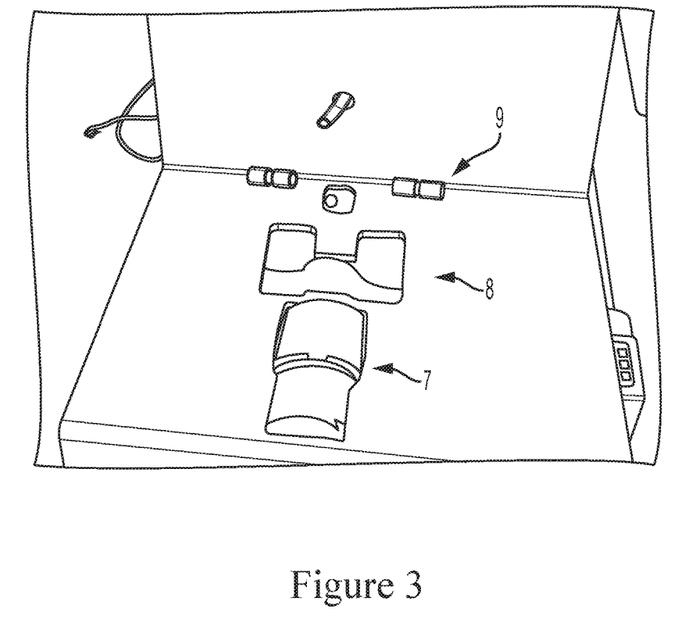
FIG. 3 shows a representative platform of a device that supports a reaction vessel (which has been removed from the view).
Figure 4:
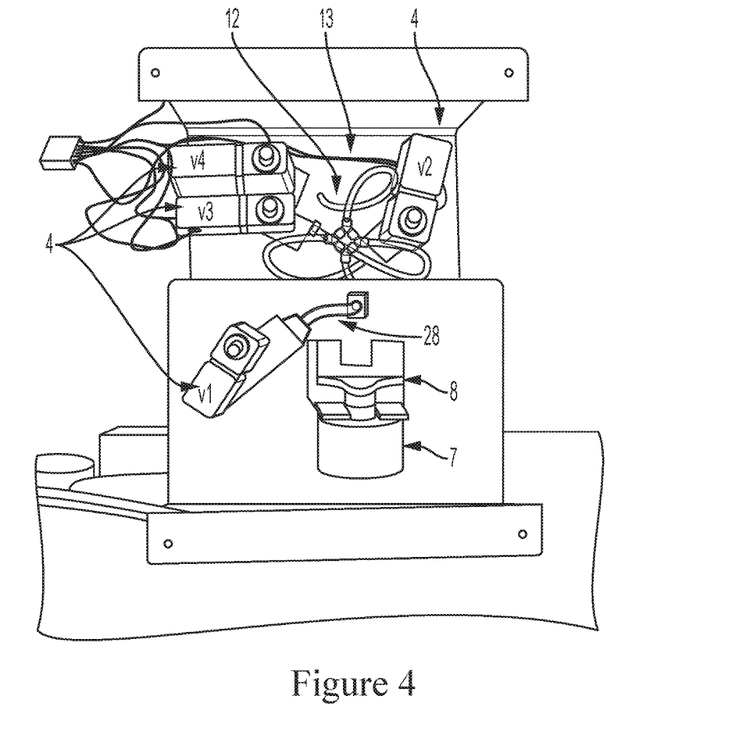
FIG. 4 shows an underneath view of a representative device.

The present disclosure provides liquid dispensing devices. The liquid dispensing devices comprise a wash buffer reservoir, at least one reagent reservoir, multiple reservoir control valves, an optional central pump, an electronic control board, a reaction vessel that comprises one or more baffles, a waste tray, and a motorized cam. FIG. 1 shows a representative liquid dispensing device having a wash buffer reservoir (1), reagent reservoirs (2 and 3), and a reaction vessel (5). FIG. 2 shows a representative liquid dispensing device showing a wash buffer reservoir (1), reagent reservoirs (2, 3), a reaction vessel (5), a first port of the reaction vessel (6), and a reaction vessel control valve (23). FIG. 3 shows a representative liquid dispensing device in which the reaction vessel has been removed showing a geared motor (7), cam (8), and reaction vessel clips (9). FIG. 4 shows the underside of a representative liquid dispensing device showing four reservoir control valves (4), a geared motor (7), a cam (8), a multi-way connector (12), and various connection tubing (13) and wiring.

In some embodiments, the wash buffer reservoir (1) serves as a chamber into which a wash buffer is poured. Any wash buffer can be used. The wash buffer reservoir can be of any shape and size, but is generally designed to hold from about 50 ml to about 500 ml, from about 100 ml to about 400 ml, or from about 200 ml to about 300 ml of liquid. The wash buffer reservoir also comprises a port (not shown), which serves as an opening into which the wash buffer can leave the wash buffer reservoir. The port can be located anywhere in the bottom of the wash buffer reservoir. In some embodiments, the port is located on the bottom of the wash buffer reservoir at one end of the reservoir. In some embodiments, the wash buffer reservoir is designed to be removable and allow complete drainage by gradients in the floor of the tray.

In some embodiments, the device comprises at least one reagent reservoir (2, 3). In some embodiments, the device comprises two or three reagent reservoirs (i.e., a primary reagent reservoir and a secondary reagent reservoir). Each reagent reservoir serves as a chamber into which various reagents are poured. Any reagent can be used. Suitable reagents include, for example, primary and secondary antibodies used for detection. The reagent reservoirs can be of any shape and size, but are generally designed to be at least 1 cm, at least 2 cm, or at least 4 cm in height, and/or designed to contain up to 0.5 ml, up to 2 ml, up to 5 ml, up to 10 ml, up to 20 ml, or up to 50 ml of reagent. Each reagent reservoir also comprises a port (not shown), which serves as an opening into which the reagent can leave the reagent reservoir. The port can be located anywhere in the bottom of the reagent reservoir. In part because the primary and secondary reagents are generally expensive, and thus small volumes (1 to 10 ml) are usually employed.

In some embodiments, the device comprises a reaction vessel (5) which serves as a chamber into which a membrane is placed. Any membrane, including PVDF and nitrocellulose membranes, can be used. The reaction vessel may also be used to contain various buffers, such as a blocking solution, that are added for a particular protocol. The reaction vessel can be of any shape and size, but is generally designed to hold a square or rectangular piece of membrane that is from about 5 cm to about 30 cm, from about 8 cm to about 20 cm, or from about 10 cm to about 15 cm in size. The reaction vessel is also designed to hold from about 0.5 ml to about 100 ml, from about 2 ml to about 75 ml, from about 5 ml to about 20 ml, or from about 8 ml to about 20 ml of liquid. In some embodiments, the reaction vessel comprises one or a plurality of baffles. The baffles may be of any shape and may be of any length to fit inside the reaction vessel, each baffle being substantially parallel to one or more other baffles. The reaction vessel further comprises a first port (6) (see, FIG. 2), which serves as an opening into which any fluids can enter the reaction vessel from the either or both the wash buffer reservoir and/or the reagent reservoir (s). The first port can be located anywhere in the side of the reaction vessel or may simply be the opening of the reaction vessel at the top. In some embodiments, the reaction vessel comprises a second port (22) (see, FIGS. 6A, 6B, 6C, 7A, 7B, 7C, 8A, 8B, and 8C), which serves as an opening in the reaction vessel into which any fluids that are within the reaction vessel can exit the reaction vessel. In some embodiments, the second port of the reaction vessel is located on the bottom of the reaction vessel at one end of the reaction vessel. The baffles also retain the membrane in the fluid area while stopping it from obstructing the second port in the reaction vessel. In some embodiments, the reaction vessel is asymmetric in regard to the second port and axis of rotation of the reaction vessel. In some embodiments, the reaction vessel comprises a plurality of analysis sections, which can each comprise a separate membrane. The reaction vessel can be made out of low friction plastic or a low friction plastic strip is adhered to its bottom base to interact with the cam. The reaction vessel design is not limited to that in any of the figure disclosed herein; other designs are possible which may have smaller or larger surface area and volume, or contain a cylinder of material that acts as a dispersal mechanism for low (<5 ml) of liquid, or contain multiple chambers for incubating membranes of different size or number. In some embodiments, the reaction vessel can be held in place by one or more reaction vessel clips (9) (see, FIG. 3).

The wash buffer reservoir and the at least one reagent reservoir are each in fluid communication with the reaction vessel. Thus, fluids may flow from the wash buffer reservoir to the reaction vessel, and can do so merely by gravitational forces in devices without a central pump. Likewise, fluids may flow from the at least one reagent reservoir to the reaction vessel, and can do so merely by gravitational forces in devices without a central pump. Fluids leave the wash buffer reservoir and the at least one reagent reservoir through their respective ports, as described above. The fluid(s) leaving the wash buffer reservoir and/or the at least one reagent reservoir enter the reaction vessel through the first port of the reaction vessel. Each port of the wash buffer reservoir and the at least one reagent reservoir are in fluid communication via tubing with the first port of the reaction vessel. In some embodiments, the fluid communication is carried out by tubing. In some embodiments, each of the tubing is about ⅛ inch internal diameter and about 3/16 inch outside diameter. Any tubing can be used. In some embodiments, the tubing is smoothly contoured so that resistance is not increased by kinks. FIG. 4 shows tubing (13) connecting one portion of the device to another portion of the device.

The flow of fluid from either or both of the wash buffer reservoir and the at least one reagent reservoir to the reaction vessel is controlled with one or more reservoir control valves (4), and the optional central pump (27). The reservoir control valve for the wash buffer reservoir may control the opening and closing of the port of the wash buffer reservoir. Alternately, while the port of the wash buffer reservoir may always be open, the reservoir control valve for the wash buffer reservoir may be an in-line component of the tubing from the wash buffer reservoir to the reaction vessel, and thus control the flow of fluid once in the tubing. Likewise, the reservoir control valve(s) for the at least one reagent reservoir(s) and the optional central pump may control the opening and closing of the port(s) of the reagent reservoir(s). Alternately, while the port of the reagent reservoir(s) may always be open and the optional central pump operating, the reservoir control valve for the at least one reagent reservoir(s) may be in-line component(s) of the tubing from the at least one reagent reservoir to the reaction vessel, and thus control the flow of fluid once in the tubing. The optional central pump is in electronic communication with the control board and can act to pull or push fluid through the various ports and tubing in the device. The central pump may also be in communication with a power source.

In some embodiments (such as, but not limited to, devices without a central pump), the port of the at least one reagent vessel and the port of the wash buffer reservoir are both at least 0.5 cm higher, at least 1 cm higher, at least 2 cm higher, at least 3 cm higher, at least 4 cm higher, or at least 5 cm higher than each of the respective reservoir control valves. In some embodiments, each of the reservoir control valves are at least 0.5 cm higher, at least 1 cm higher, at least 2 cm higher, at least 3 cm higher, at least 4 cm higher, or at least 5 cm higher than the first port of the reaction vessel.

In some embodiments, the tubing leaving the respective reservoir control valves (i.e., tubing from the wash buffer reservoir leading to its reservoir control valve, and the tubing from each of the reagent reservoir(s) leading to its/their reservoir control valve(s); and leaving the reservoir control valves) converge to a multi-way connector (12) (see, FIG. 4). The multi-way connector is in fluid communication with the optional central pump and reaction vessel by additional tubing which enters the reaction vessel by the first port of the reaction vessel or simply disposes its contents into the opening for the reaction vessel. In some embodiments, the multi-way connector is a 4-way connector. In some embodiments, the multi-way connector that receives the reservoir solutions is mounted at an angle and close to the reaction vessel. In this manner, there is a lower probability of cross contamination between different solutions for different steps in the procedures because the tubing connecting the multi-way connector and the reaction vessel is short and it is tilted downward. Whichever fluid is flowing through the connector will continue to flow until all fluid has moved into the reaction vessel because the connector, in particular the portion of the connector leading to the reaction vessel, is angled downwards into the reaction vessel.

In some embodiments, the waste tray serves as a chamber into which the fluid from the reaction vessel drains. The waste tray can be of any shape and size, but is generally designed to hold from about 100 ml to about 2000 ml, from about 150 ml to about 1500 ml, from about 200 to about 800 ml, or from about 250 ml to about 400 ml of fluid. In some embodiments, the waste tray comprises a port, which serves as an opening into which the fluid from the reaction vessel (through the second port thereof) can enter the waste tray. The port can be located anywhere in the top portion of the waste tray. The waste tray is in fluid communication with the reaction vessel by tubing. In some embodiments (such as, but not limited to, devices without a central pump), the second port of the reaction vessel is at least 0.5 cm higher, at least 1 cm higher, at least 2 cm higher, at least 3 cm higher, at least 4 cm higher, or at least 5 cm higher than the port in the waste tray.

In some embodiments, the flow of fluid from the reaction vessel to the waste tray reaction is controlled with a reaction vessel control valve (23) (see, FIG. 2). The reaction vessel control valve may control the opening and closing of the second port of the reaction vessel. Alternately, while the second port of the reaction vessel may always be open, the reaction vessel control valve may be an in-line component of the tubing from the reaction vessel to the waste tray, and thus control the flow of fluid once in the tubing.

The devices further comprise a cam (8), powered by a geared motor (7), in physical connection with the reaction vessel. The cam is designed to tilt the reaction vessel from one to four times, or twice, for every rotation of the motor output. The cam can also use 1, 2, 3, 4, 5 or more high points for tilting. The motor output rotates at about 40 rpm with 12 V power and, therefore, the tilting up and down cycle is performed twice per revolution and 80 times per minute, but the frequency is not limited to this rate and can also be higher or lower. The cam can be made out of low friction plastic which interacts with the underside of the reaction vessel which can also be interfaced with low friction plastic and, thus, create a low friction tilting mechanism. In some embodiments, the cam comprises an off-set shape. In some embodiments, the reaction vessel is tethered at one end and is positioned to rock up and down at the distal end (i.e., non-tethered end) by interaction with the cam. Thus, in some embodiments, the reaction vessel is designed to tilt back and forth through a small angle with an axis on one end of the vessel. The tilting amplitude is helpful for a good waveform to maintain appropriate liquid movement across the membrane which improves detection of analytes and reduces background signals. In some embodiments, the reaction vessel further comprises a cylinder that moves up and down with the action of the cam. A simple geared motor with low friction plastic cam creates a low friction tilting mechanism which is programmed to be on at the beginning of the routine and off at the end. Thus, an on/off control switch for tilting need not be required. The motor is in electronic communication with the control board and with a power source (not shown).

Figure 5A:
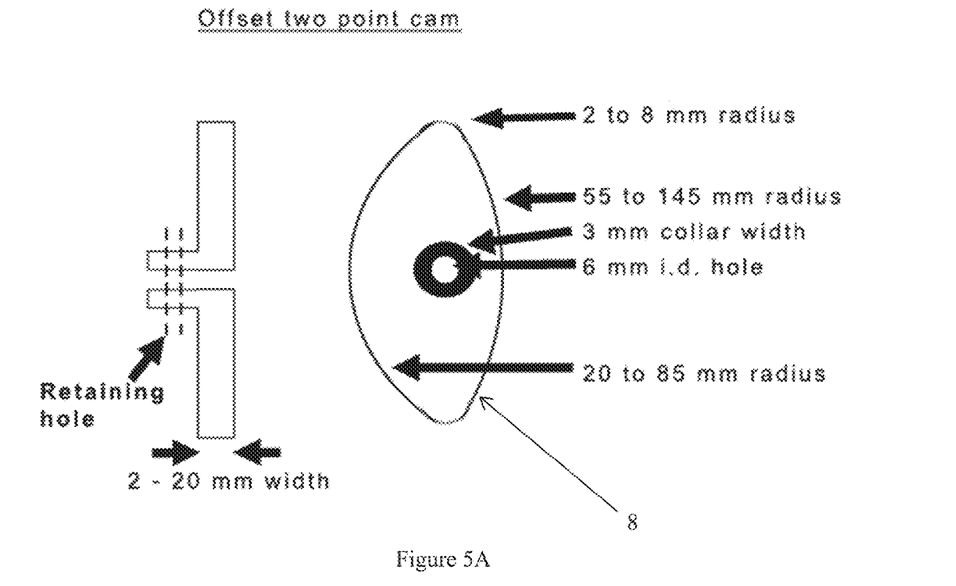
FIGS. 5A and 5B show representative cam designs and the reaction vessel wave indicating asymmetric and symmetric two point cam design.
Figure 5B:
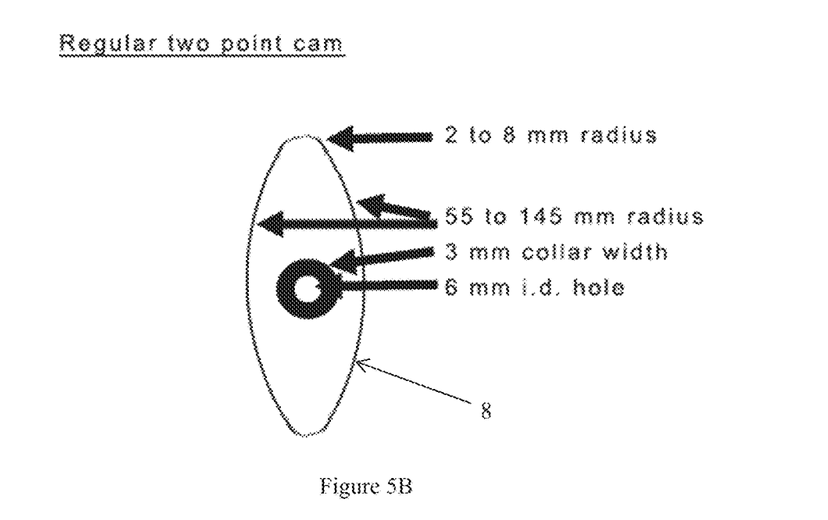

FIGS. 5A and 5B show representative cam designs and the reaction vessel wave indicating asymmetric and symmetric two point cam design. Each of the cams can be from about 2 to about 20 mm in width and can have a variety of radius designs from which to select, depending upon the degree of tilt desired for the reaction vessel. The asymmetric design creates good drainage and a good waveform by spending more time in the tilted up position and a rapid drop to the lowest level which creates a wave in the liquid which can be desirable compared to constant tilting without a wave. The asymmetric cam can be made in various shapes such as: the two high points having a radius which is 3 mm wider than the second highest point which is at right angles to them, the second highest point having a radius which is 2 mm wider than the lowest point which is opposite the second highest point. If the reaction tray is considered in a reference location when it is horizontal (no tilt), then the high point of the tilt is 9 mm above horizontal, the second high point is 2 mm above horizontal and the lowest point is 2 mm below horizontal. The design of the cam allow these different tilt amplitudes to occur. Other radii can be used to create different tilting amplitudes and frequencies.

FIGS. 6A, 6B, 6C, 7A, 7B, 7C, 8A, 8B, and 8C show representative designs for the reaction vessel and how it interacts with other components in the liquid dispensing device. In some embodiments, the introduction of fluid is from the multi-way connector which directs fluid into the reaction vessel from above (where the first port is actually the opening to the reaction vessel). The membrane and fluid are agitated in the reaction vessel by tilting, and the baffles keep the membrane out of the way of the second port drain which is located at the axis of rotation. Because of the cam shape, the reaction vessel can be tilted up at its distal end for the majority of the tilting cycle, which aids the drainage of fluid to the waste tray.

Figure 6A:
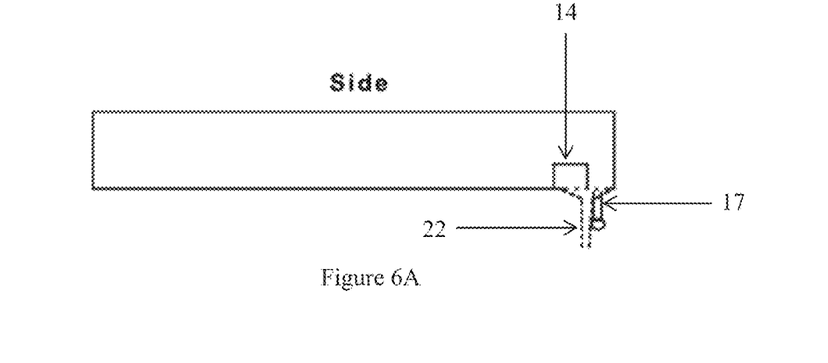
FIGS. 6A, 6B, and 6C show a first representation of a reaction vessel design.
Figure 6B:
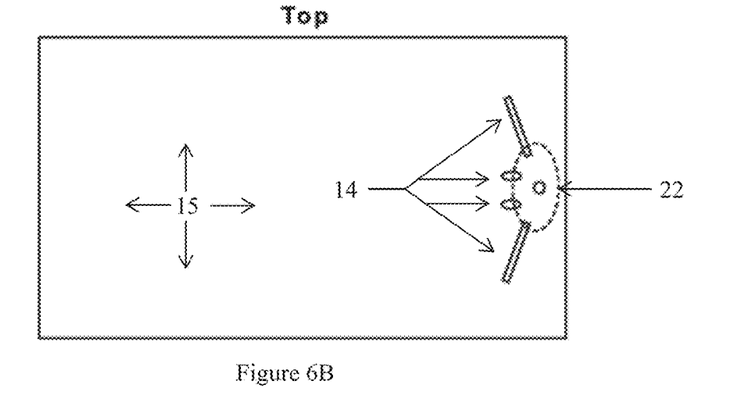
Figure 6C:
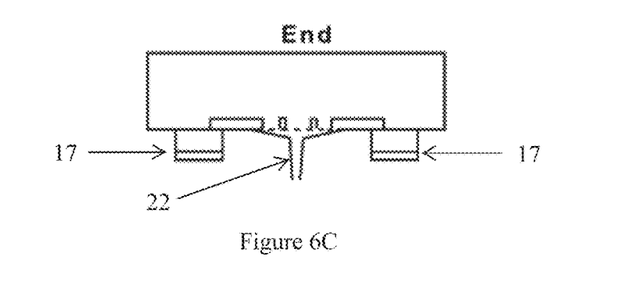

Referring to FIGS. 6A, 6B, and 6C, a first reaction vessel design is shown. The basic design has a flat lower surface with baffles (14) separating the membrane probing area (15) from the second port (22) of the reaction vessel, and the axis of rotation is in the location of the tray retaining clips next to the chassis bulk head end. The tray tilts down only 1 or 2 mm at its distal end and upward by 8 to 10 mm. Other tilting angles and amplitudes are possible and work well. In some embodiments, the reaction vessel can comprise one or more clips in legs (17), as shown on the bulk head end. Other reaction vessel designs are possible which allow for smaller volumes of SAR, different sizes and numbers of membranes (e.g., the use of a plastic cylinder as a dispersal mechanism for small volumes (see, FIGS. 7A, 7B, and 7C) or using, for example, fifteen mini-chambers for incubating strips of 0.3 cm×8 cm within one reaction vessel (see, FIGS. 8A, 8B, and 8C).

Figure 7A:
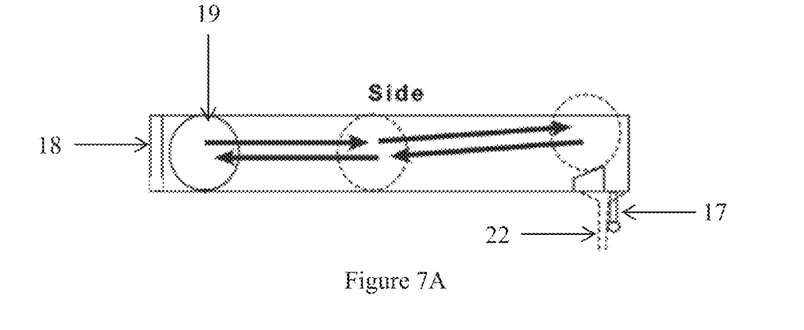
FIGS. 7A, 7B, and 7C show a second representation of a reaction vessel design.
Figure 7B:
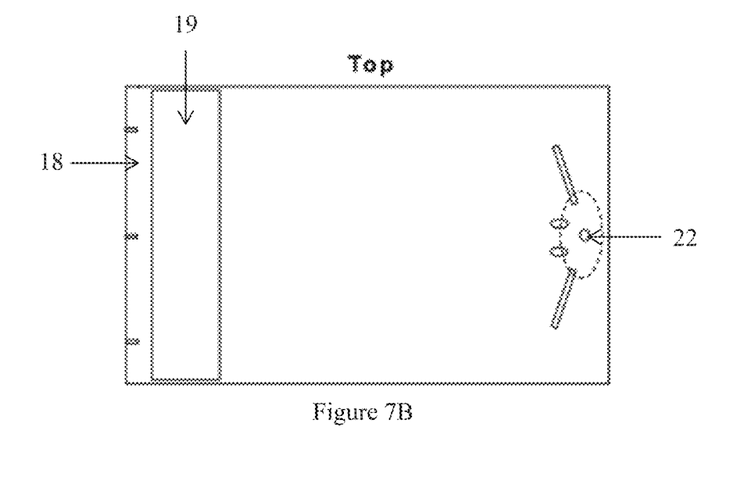
Figure 7C:
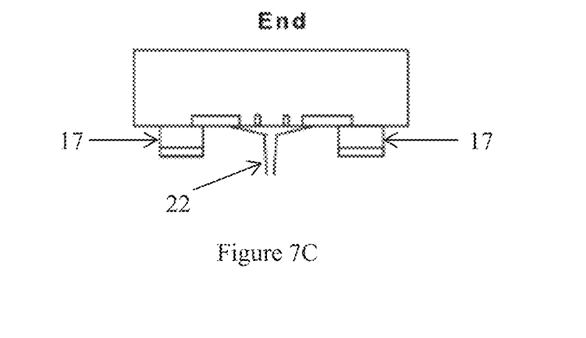

Referring to FIGS. 7A, 7B, and 7C, a second reaction vessel design is shown. The small volume of SAR is necessary in some cases where SAR is limiting (e.g., with expensive antibody solutions or when using mouse serum). This design incorporates a plastic cylinder (19) which is suitably heavy and of sufficient diameter to roll up and down the reaction vessel on top of the membrane when the vessel is inclined up and down. Liquid volumes as low as 1 ml of SAR can be evenly spread across a normal sized membrane thus saving valuable reagent. In some embodiments, separators (18) are located at the distal end to stop surface tension causing the cylinder to adhere to the wall of the vessel.

Figure 8A:
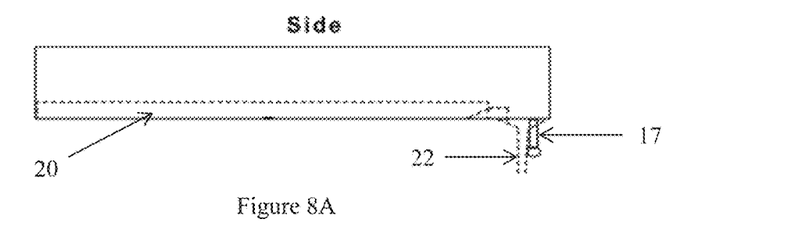
FIGS. 8A, 8B, and 8C show a third representation of a reaction vessel design.
Figure 8B:
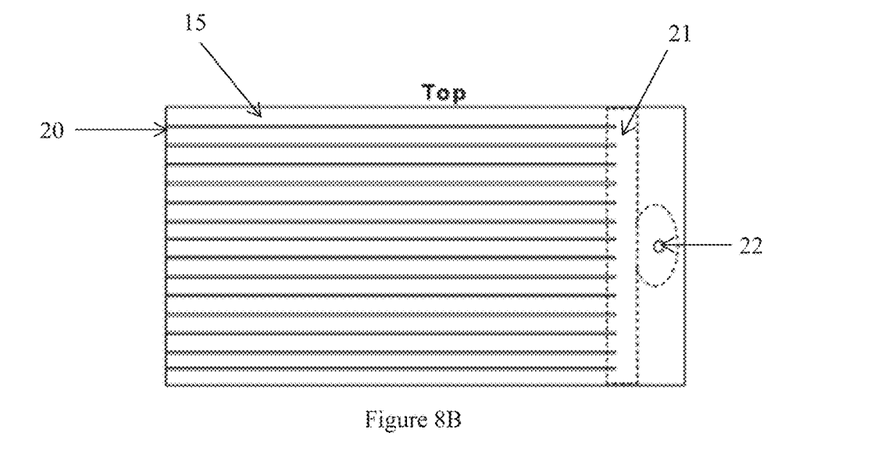
Figure 8C:
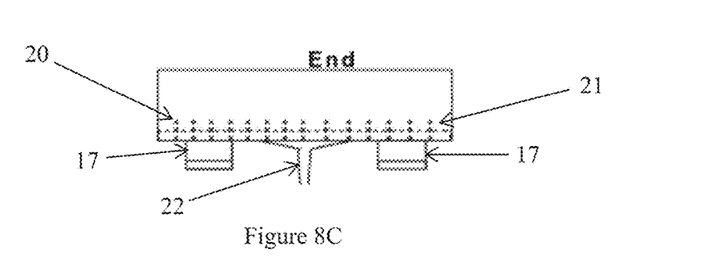

Referring to FIGS. 8A, 8B, and 8C, a third reaction vessel design is shown. In some situations, the operator may need to measure the activity of antibodies in very small volumes (e.g., 200 µl or less). In this case, the reaction vessel has individual mini-chambers separated by walls (20), and optionally a dam (21) to stop the SAR solution moving out of a mini-chamber and mixing with the others. During a wash step, a large volume (e.g., 20 ml or more) of wash buffer flows over the dam and into the whole reaction vessel and immediately drains out of the second port, thus not allowing time for SARs to contaminate each other's chamber.

Figure 9:
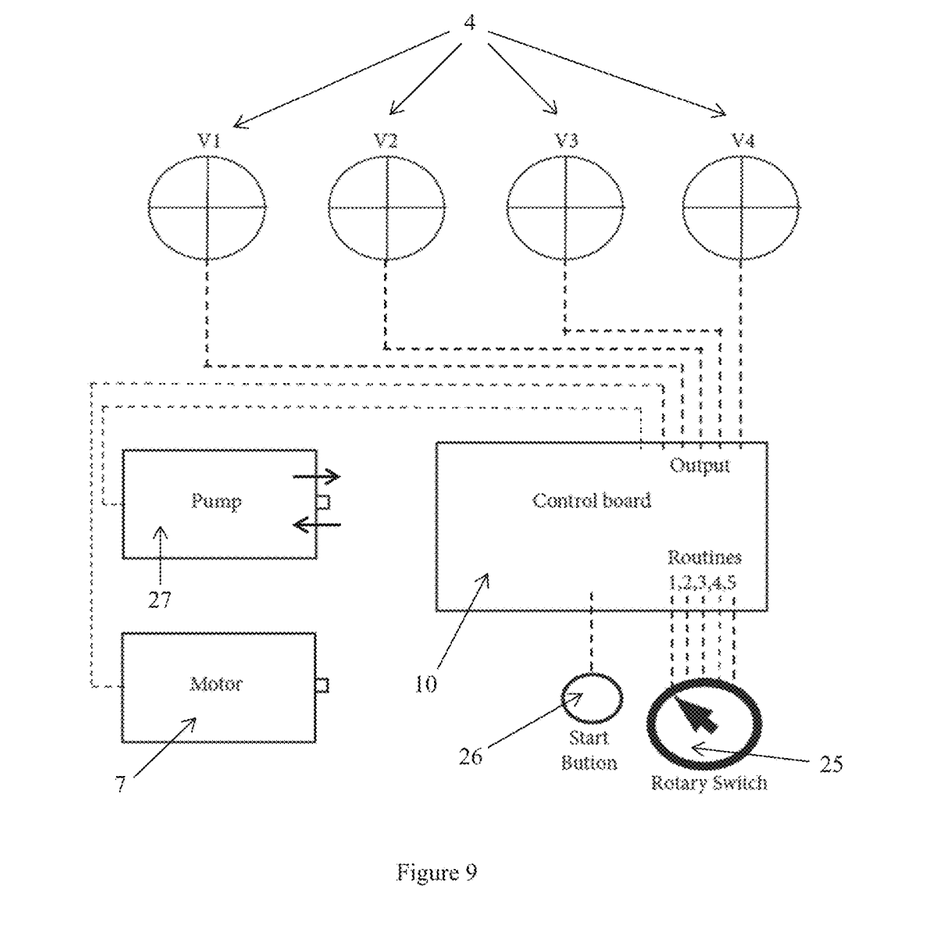
FIG. 9 shows a representative electrical layout of a device, indicating a simplistic design of a control board, valves, and motor control.

In each of the embodiments disclosed herein, each control valve is in electrical communication with an electronic control board (10) (see, FIG. 9), which comprises a start button (26), which can be utilized to start a particular routine, and a rotary switch (25), which can be used to select a particular routine. Thus, the electronic control board controls the opening and closing of each control valve (4) (see V1, V2, V3, V4, P1 in FIG. 9) and fluid pumping and controls the length of time that each control valve is opened, and thus the volume of fluid being transported. In some embodiments, the electronic control board is commercially available, such as, for example, Arduino Uno or Mega, or the like. In some embodiments, one or more of the control valves may be operated manually. In some embodiments, the electronic control board contains software that is programmable to carry out particular routines to control the sequence of control valve opening and closing and the length of time each control valve is opened. In some embodiments, the control board will have a power switch to control the operation of the motor for the cam. In some embodiments, the electronic control board is programmable to control the speed of the motorized cam. In some embodiments, the electronic control board further comprises a communication port, such as a USB port for ISO9000 type compliance, for another device. In some embodiments, the USB port is included for ISO9000-type reporting of the device's events during a particular procedure. In some embodiments, the electronic control board comprises Bluetooth remote control capability, which can allow for remote programming and control of the device.

The control software program for the control board is very flexible with all steps being able to be modified and reprogrammed. However, a short list of routines can cover a majority of practical procedures. Thus, a basic program design which incorporates this short list can simplify the interface with the end user by providing several push buttons or a rotary switch with several positions. For example, one routine provides the opportunity to treat the membrane with just two reagents (e.g., wash and primary reagent) which gives flexibility for other applications such as probing with a pre-labeled primary reagent. The pre-programmed routines can be varied in time and number of steps.

The devices disclosed herein can be compact and portable. In some embodiments, the entire device is less than 30 cm×50 cm, less than 20 cm×30 cm, or less than 16 cm×24 cm, and weighs less than 10 kg, or less than 5 kg, or less than 2 kg. In some embodiments, the device is about 15 cm×about 22 cm. In some embodiments, a chassis connects each of the wash buffer reservoir, reagent reservoir(s), reaction vessel, wash tray, and cam motor and is also the exterior shell of the device. In some embodiments, the device comprises rounded corners, high sloping walls, and/or lower walls that are mainly vertical to allow close packing.

The reaction vessel is tilted with an asymmetric amplitude to create a waveform in the fluid which can be adjusted, by placement of the cam from a centered position to any one of a number of off-center placements. This allows for agitation and improved analyte detection, and also aids the draining of fluids at the end of each step.

The present disclosure also provides a system that comprises a plurality of any one or more of the devices disclosed herein. The system may be controlled by a single electronic control board which controls all valves, motors, and optional central pumps, of each device.

The present disclosure also provides methods of analyzing a membrane using a device as described herein. In some embodiments, such as a Western Blot embodiment, a wash buffer is loaded into the wash buffer reservoir. A first reagent is loaded into one of the at least one reagent reservoirs. A second reagent is optionally loaded into a different one of the at least one reagent reservoirs. The membrane and blocking reagent are placed into the reaction vessel. A routine from the electronic control board is selected and runs for a predetermined amount of time. The membrane is removed from the reaction vessel for subsequent signal development and result acquisition. For example, the operator will previously have an analyte bound-membrane from a Western Blot experiment, and will have prepared four solutions: 1) blocking reagent (20 ml), 2) wash buffer (300 ml), 3) SAR (5 ml), and 4) secondary amplifying reagent (15 ml). The operator will add the wash buffer into the wash buffer reservoir, and the primary and secondary reagents into their appropriate reagent reservoirs. Then the membrane is placed in the reaction vessel and the blocking solution is poured over it. The desired routine is chosen by pressing a switch and the routine runs without interruption. The operator can return after about 4 hours (or when the routine ends) or the full length of time of another routine and removes the membrane for subsequent signal development and result acquisition by any of the known methods. The operator can remove excess wash buffer remaining in the wash buffer reservoir and apply nanopure water to any of the reservoirs and run a programmed wash routine which preserves the components for future use.

Figure 10:
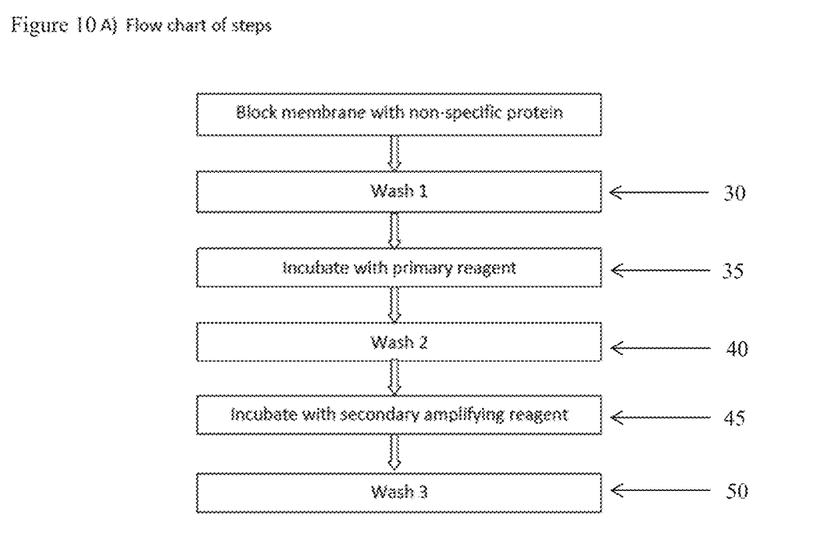
FIGS. 10A and 10B show a representative flow chart of standard operating procedure for using a device.

Referring to FIG. 10A, a representative flow chart of standard operating procedure with variable aspects is shown. The flow chart represents typical steps in a standard operating procedure. For example, a blocked membrane is washed (30), incubated with primary reagent (35), washed (40), incubated with secondary reagent (45), and washed again (50). FIG. 10B shows a typical range of variations in Western blots and an exemplary routine programmed into the controller.

In order that the subject matter disclosed herein may be more efficiently understood, examples are provided below. It should be understood that these examples are for illustrative purposes only and are not to be construed as limiting the claimed subject matter in any manner.

EXAMPLES

Example 1: Western Blot (Actual Example)

A typical western blot procedure was performed. First, a membrane was prepared which contained the adhered proteins, which were separated by electrophoresis using an SDS containing polyacrylamide gel. Several protein containing samples were prepared; ten lanes were loaded with: 1) molecular weight marker (MWM) (lane 1); 2) various amounts of purified recombinant RhoA protein (RH01) (lanes 2 to 7); and 3) various amounts of platelet cell protein extract (lanes 8, 9, and 10). Electrophoresis was performed at 150V for 1.5 hours. The gel was placed into blotting buffer containing 25 mM Tris base, 180 mM glycine, and 15% methanol in nanopure water to equilibrate. The gel was then sandwiched between filter paper and the membrane on the positively charged side of the gel (SDS surrounded proteins migrate towards the positive terminal) and electroblotting was performed at 350 mA for 45 minutes. The membrane was transferred to a device as set forth herein and the following protocol was carried out.

Four solutions were prepared: 1) Phosphate Buffered Saline plus Tween 20 (PBST): 1.44 g $Na_2HPO_4$, 0.24 g $KH_2PO_4$, 0.20 g KCl, 8 g NaCl, 995 ml nanopure water; mixed until dissolved and pH to 7.4 with 1M HCl; 2) Blocking Solution: 1 g (5% w/v) dry milk powder in 20 ml of PBST; 3) Primary Antibody in PBST: 5 µl of anti-RhoA (Cat. #ARH04 from Cytoskeleton Inc., CO, USA) in 5 ml of PBST; and 4) Secondary Antibody (horse radish peroxidase labeled, HRP) in PBST: 1 µl of anti-mouse IgG HRP (Cat. #115-035-164 from Jackson Immunoresearch Labs, PA, USA) in 20 ml of PBST.

The device was turned on and the rotary knob turned to the protocol number 1 which is a normal routine for Western Blots. All valves were in the closed position at the start of the routine. Three hundred (300) ml of PBST was poured into the wash buffer reservoir. Twenty (20) ml of blocking solution was poured into the reaction vessel and the membrane was added to this solution. The primary antibody (in 5 ml solution) was poured into the first reagent reservoir, and the secondary antibody (in 20 ml solution) was poured into a second reagent reservoir. The routine was started by pressing the start button.

Figure 11:
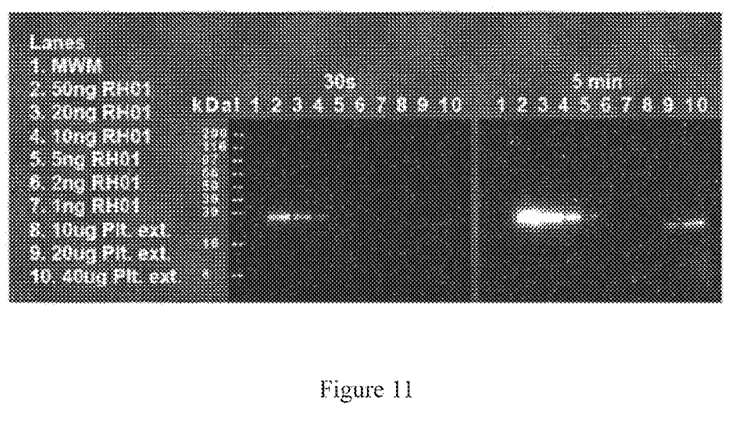
FIG. 11 shows a representative image of a PVDF-membrane, processed using a device described herein, which was placed into a dark camera chamber.

About four hours later, the membrane was removed from the reaction vessel and placed on a paper towel. The membrane was dabbed dry and placed on a piece of 4 mil polythene, to which 1 ml of HRP detection reagent (e.g. Cat. #34076 from ThermoFisher Scientific Inc., MA, USA) was pipetted on to the membrane to develop the chemiluminescent signal. Another layer of polyurethane was sandwiched on top. The polyurethane-membrane sandwich was placed into a dark camera chamber and an image was taken (see, FIG. 11 for results). Detection of purified recombinant RhoA at 28 kDal molecular weight with a 10 ng detection limit was observed at a 30 second exposure, and down to 5 ng at a 5 minute exposure. The detection of native RhoA at 21 kDal molecular weight was observed where approximately 10 ng of RhoA was detected in 40 µg of platelet cell extract. The dark background was indicative of very good washing of the membrane between incubation steps.

Routine Steps:

The first versions contains what the operator sees, whereas the second version contains the software program valve timings.

Physical Routine
1. Tilt mechanism starts;
2. Block for one hour;
3. Wash in PBST once for 3 min;
4. Primary reagent for one hour;
5. Wash in PBST for 5 min (repeat for 3 times total);
6. Secondary reagent for one hour;
7. Wash in PBST for 5 min (repeat for 5 times total);
8. Remove membrane and develop signal with chemiluminescence substrate.

Software Routine Valve Commands

| Starting Time | Routine 1 (1-1-1) |
|---|---|
| 00:00:00.0 | Motion platform On and Open V1(drain) |
| 00:00:00.0 | Wait for 3600 sec. |
| 01:00:00.0 | Open V1 (drain) for 10.0 sec. |
| 01:00:10.0 | Close V1 |

-continued

| Starting Time | Routine 1 (1-1-1) |
|---|---|
| 01:00:11.0 | Open V2 (wash) and optional pump (P1) on for 12.0 sec. |
| 01:00:23.0 | Close V2 and P1 off |
| 01:00:24.0 | Wait for 180 sec. |
| 01:03:24.0 | Open V1 (drain) for 10.0 sec. |
| 01:03:34.0 | Close V1 |
| 01:03:35.0 | Open V3 (primary antibody) and optional pump (P1) on for 10.0 sec. |
| 01:03:45.0 | Close V3 and pump off |
| 01:03:46.0 | Wait for 3600 sec. |
| 02:03:46.0 | Open V1 (drain) for 10.0 sec. |
| 02:03:56.0 | Close V1 |
| 02:03:57.0 | Open V2 (wash) and optional pump (P1) on for 14.0 sec. |
| 02:04:11.0 | Close V2 and pump off |
| 02:04:12.0 | Wait for 300 sec. |
| 02:09:12.0 | Open V1 (drain) for 10.0 sec. |
| 02:09:13.0 | Close V1 |
| 02:09:14.0 | Open V2 (wash) and optional pump (P1) on for 14.0 sec. |
| 02:09:28.0 | Close V2 and pump off |
| 02:09:29.0 | Wait for 300 sec. |
| 02:14:29.0 | Open V1 (drain) for 10.0 sec. |
| 02:14:39.0 | Close V1 |
| 02:14:30.0 | Open V2 (wash) and optional pump (P1) on for 14.0 sec. |
| 02:14:44.0 | Close V2 and pump off |
| 02:14:44.0 | Wait for 300 sec. |
| 02:19:44.0 | Open V1 (drain) for 10.0 sec. |
| 02:19:54.0 | Close V1 |
| 02:19:55.0 | Open V4 (secondary antibody) and optional pump (P1) on for 10.0 sec. |
| 02:21:05.0 | Close V4 and pump off |
| 02:21:05.0 | Wait for 3600 sec. |
| 03:21:05.0 | Open V1 (drain) for 10.0 sec. |
| 03:21:15.0 | Close V1 |
| 03:21:16.0 | Open V2 (wash) and optional pump (P1) on for 17.0 sec. |
| 03:21:33.0 | Close V2 and pump off |
| 03:21:33.0 | Wait for 300 sec. |
| 03:26:33.0 | Open V1 (drain) for 10.0 sec. |
| 03:26:43.0 | Close V1 |
| 03:26:44.0 | Open V2 (wash) and optional pump (P1) on for 17.0 sec. |
| 03:27:01.0 | Close V2 and pump off |
| 03:27:02.0 | Wait for 300 sec. |
| 03:32:02.0 | Open V1 (drain) for 10.0 sec. |
| 03:32:12.0 | Close V1 |
| 03:32:13.0 | Open V2 (wash) and optional pump (P1) on for 17.0 sec. |
| 03:32:30.0 | Close V2 and pump off |
| 03:32:30.0 | Wait for 300 sec. |
| 03:37:30.0 | Open V1 (drain) for 10.0 sec. |
| 03:37:40.0 | Close V1 |
| 03:37:41.0 | Open V2 (wash) and optional pump (P1) on for 17.0 sec. |
| 03:37:58.0 | Close V2 and pump off |
| 03:37:58.0 | Wait for 300 sec. |
| 03:42:58.0 | Open V1 (drain) for 10.0 sec. |
| 03:43:08.0 | Close V1 |
| 03:43:09.0 | Open V2 (wash) and optional pump (P1) on for 17.0 sec. |
| 03:43:26.0 | Close V2 and pump off |
| 03:43:26.0 | Wait for 300 sec. |
| 03:48:26.0 | Routine 1 (1-1-1) finished. |

Closed all valves and turned Motion platform off

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, and the like) cited in the present application is incorporated herein by reference in its entirety.

What is claimed is:

1. A liquid dispensing device comprising:
a wash buffer reservoir and at least one reagent reservoir, each reservoir comprising a reservoir control valve, wherein each reservoir control valve is in electrical communication with an electronic control board;
a reaction vessel in fluid communication with the wash buffer reservoir and the at least one reagent reservoir, wherein the reaction vessel comprises a first port and a second port, and wherein the reaction vessel comprises two baffles, each one of said baffles is disposed on either side of the second port;
wherein the one or more baffles separate a membrane probing area from the second port of the reaction vessel and retain the membrane in the reaction vessel and stop the membrane from obstructing the second port of the reaction vessel:
a waste tray in fluid communication with the reaction vessel; a motorized, off-set asymmetric cam in physical connection with the reaction vessel configured to cause a tilting motion; and
a central pump in electrical communication with the electronic control board and in fluid communication with the wash buffer reservoir and at least one reagent reservoir.

2. The device of claim 1, wherein each of the wash buffer reservoirs and at least one reagent reservoir comprise a port which is in fluid communication with a first the first port in the reaction vessel.

3. The device of claim 2, wherein each of the port of the wash buffer reservoir and the port of the at least one reagent reservoir are in fluid communication by tubing with the first port of the reaction vessel.

4. The device of claim 2, wherein each reservoir control valve either controls the ports of the wash buffer reservoir and the at least one reagent reservoir, or controls the fluid communication within the respective tubing.

5. The device of claim 3, wherein the tubing from the wash buffer reservoir and the tubing from the at least one reagent reservoir are in fluid communication with a multi-way connector and the central pump.

6. The device of claim 5, wherein the multi-way connector is in fluid communication with the reaction vessel by tubing.

7. The device of claim 1, wherein a port in the waste tray is in fluid communication with the second port in the reaction vessel by tubing.

8. The device of claim 7, wherein a reaction vessel control valve either controls the second port of the reaction vessel, or controls the fluid communication within the tubing from the reaction vessel to the waste tray.

9. The device of claim 1, wherein the electronic control board controls the opening and closing of each control valve, turns the central pump on and off, and controls the length of time that each control valve is opened.

10. The device of claim 9, wherein the electronic control board contains software that is programmable to control the sequence of control valve opening and closing and the length of time each control valve is opened.

11. The device of claim 1, wherein the electronic control board is programmable to control the speed of the motorized cam.

12. The device of claim 1, wherein the reaction vessel is tethered at one end and is positioned to rock up and down at the distal end by interaction with the cam.

13. The device of claim 1, further comprising a communication port for ISO9000 compliance.

14. The device of claim 1, wherein the electronic control board comprises Bluetooth remote control capability.

15. The device of claim 1, wherein the reaction vessel is asymmetric in regard to the second port and axis of rotation of the reaction vessel.

16. The device of claim 1, wherein the reaction vessel further comprises a cylinder that moves up and down with the action of the cam.

17. The device of claim 1, wherein the reaction vessel comprises a plurality of analysis sections.

18. The device of claim 1, wherein the entire device is less than 30 cm×50 cm and weighs less than 5 kg.

19. The device of claim 1, wherein each of the tubing is about 1/8 inch internal diameter and about 3/16 inch outside diameter.

20. The device of claim 1, wherein each of the at least one reagent reservoirs comprises an interior capable of holding up to 20 ml of reagent.

21. The device of claim 1, wherein a chassis connects each of the wash buffer reservoir, reagent reservoir(s), reaction vessel, wash tray, and cam motor and is also the exterior shell of the device.

22. A method of analyzing a membrane using the device of claim 1 comprising:
   loading a wash buffer into the wash buffer reservoir;
   loading a first reagent into one of the at least one reagent reservoirs;
   loading a second reagent into a different one of the at least one reagent reservoirs;
   loading the membrane and blocking reagent into the reaction vessel;
   selecting a routine from the electronic control board; and
   removing the membrane from the reaction vessel for subsequent signal development and result acquisition.

\* \* \* \* \*